(12) United States Patent
Brady et al.

(10) Patent No.: US 10,351,751 B2
(45) Date of Patent: Jul. 16, 2019

(54) WELLBORE SEALANT USING NANOPARTICLES

(71) Applicant: SCHLUMBERGER TECHNOLOGY CORPORATION, Sugar Land, TX (US)

(72) Inventors: Dominic Joseph Brady, Dhahran (SA); Mohan Kanaka Raju Panga, Sugar Land, TX (US); Wael Abdallah, Al-Khobar (SA)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 181 days.

(21) Appl. No.: 15/225,933

(22) Filed: Aug. 2, 2016

(65) Prior Publication Data
US 2018/0037797 A1 Feb. 8, 2018

(51) Int. Cl.
*E21B 33/138* (2006.01)
*C09K 8/42* (2006.01)
(Continued)

(52) U.S. Cl.
CPC ............... *C09K 8/426* (2013.01); *C09K 8/04* (2013.01); *C09K 8/516* (2013.01); *E21B 21/003* (2013.01);
(Continued)

(58) Field of Classification Search
CPC ............ E21B 33/138; C09K 8/02; C09K 8/50
See application file for complete search history.

(56) References Cited

U.S. PATENT DOCUMENTS

| 4,743,854 A | 5/1988 | Vinegar et al. |
| 8,657,005 B2* | 2/2014 | Entchev ............... C09K 8/508 |
| | | 166/285 |

(Continued)

FOREIGN PATENT DOCUMENTS

CN 104504192 A 4/2015

OTHER PUBLICATIONS

Search Report and Written Opinion of International Patent Application No. PCT/US2017/041822 dated Dec. 26, 2017, 13 pages.

*Primary Examiner* — Kenneth L Thompson (57) ABSTRACT

A wellbore is internally sealed using nanoparticles. Permeability properties are determined for a particular formation, along with its pore throat size distribution. A wellbore internal sealant (nanoparticle treatment fluid) is designed based on the determined permeability properties and pore throat size distribution. The nanoparticle treatment fluid is introduced into the formation. Pore throats within the formation are plugged by nanoparticles in the nanoparticle treatment fluid. Internal sealing reduces leak-off from filtercake damage, and also eliminates build-up of surface filtercake. Sealing the pore-structure of a particular wellbore zone alleviates the need for additional lost circulation material, resulting in a very thin filtercake and significantly reducing the chance of differential sticking. Oil-based muds can be replaced with water-based equivalents. The nanoparticle treatment fluid results in a permanent reduction in formation permeability, and therefore is particularly suitable for wells that will be stimulated using perforations, matrix acidizing, or fracturing techniques.

19 Claims, 4 Drawing Sheets

(51) Int. Cl.
*C09K 8/04* (2006.01)
*E21B 21/00* (2006.01)
*E21B 33/14* (2006.01)
*E21B 49/00* (2006.01)
*G01N 15/08* (2006.01)
*G01V 3/32* (2006.01)
*C09K 8/516* (2006.01)

(52) U.S. Cl.
CPC ............ *E21B 33/138* (2013.01); *E21B 33/14* (2013.01); *E21B 49/00* (2013.01); *G01N 15/08* (2013.01); *G01V 3/32* (2013.01); *C09K 2208/10* (2013.01); *E21B 49/008* (2013.01)

(56) References Cited

U.S. PATENT DOCUMENTS

| | | | | |
|---|---|---|---|---|
| 8,783,352 B2 * | 7/2014 | Chenevert | ............ | C09K 8/032 166/293 |
| 9,915,123 B2 * | 3/2018 | Bennetzen | ............ | E21B 33/138 |
| 9,920,233 B2 * | 3/2018 | Husein | ............ | C09K 8/516 |
| 2009/0005995 A1 | 1/2009 | Tang et al. | | |
| 2009/0314549 A1 | 12/2009 | Chenevert et al. | | |
| 2012/0015852 A1 * | 1/2012 | Quintero | ............ | C09K 8/032 507/112 |
| 2012/0181033 A1 * | 7/2012 | Saini | ............ | C09K 8/265 166/308.1 |
| 2012/0245058 A1 * | 9/2012 | Monteiro | ............ | C09K 8/032 507/110 |
| 2012/0285691 A1 * | 11/2012 | Berger | ............ | C09K 8/50 166/305.1 |
| 2014/0303049 A1 * | 10/2014 | Holdsworth | ............ | C09K 8/56 507/241 |
| 2015/0315868 A1 * | 11/2015 | Fripp | ............ | E21B 33/10 166/387 |
| 2016/0009979 A1 * | 1/2016 | Husein | ............ | C09K 8/36 507/140 |
| 2018/0010435 A1 * | 1/2018 | Nguyen | ............ | E21B 43/267 |

* cited by examiner

WELLBORE SEALANT USING NANOPARTICLES

BACKGROUND

Drilling a wellbore is often performed using drilling fluid that is maintained at a density so as to create a hydrostatic pressure that exceeds the pore-pressure of connate fluids in any formation through which the wellbore penetrates. This drilling condition is known as "over-balanced" and can cause "leak-off" or "lost circulation" of the drilling fluid into the formation. Lost circulation can be a significant issue while drilling. Drilling muds typically contain particles such as calcium carbonate to restrict leak-off. The particles typically form a "filtercake" or "mudcake" on the wellbore wall that presents a low-permeability barrier to any additional losses in a given section of the wellbore. This filtercake is typically deliberately designed to be weak or low-strength so that when the well is allowed to flow back with hydrocarbons, the mudcake cleans up easily and does not restrict the flow of hydrocarbons into the wellbore. Any restriction would be considered part of the near-wellbore formation damage or reservoir "skin" and would result in a lower productivity index, which is highly undesirable for an operator. However, the fragile nature of the filtercake typically means that it is constantly reformed as it is scraped off by the passing drillstring, drill-stabilizers, or directional drilling pads.

In non-reservoir, (typically) upper regions of the wellbore where there are no recoverable hydrocarbons, it is generally desirable to seal this region permanently. This is typically achieved at several intervals by placing and cementing casing. Casing resolves the issue of leak-off and accommodates changes in mud-weight (i.e., density) for pore-pressure control. However, cementing on top of filtercake is a difficult process, and improper filtercake cleanup results in a poor quality cement bond between the formation and the casing. Where a poor bond exists, well-control issues become a risk since the poor bond can present an uncontrolled channel to the surface.

Drilling in regions with high tectonic stresses may require significant over-balance to maintain wellbore stability, while still encountering regions of significant porosity and regions of low pore-pressure such as when an area has been producing for some time or in the presence of heterogeneity. In these formations the need to counter a high level of leak-off, together with the mechanical damage to and subsequent rebuilding of the filtercake, can result in a significant volume of solids being deposited on the wellbore wall, thereby producing a thick filtercake. This can lead to "differential sticking", whereby the drillstring embeds in the filtercake material and is held in place by the differential pressure between the over-balance fluid pressure and the significantly lower formation pore-pressure. Such differential sticking causes very significant non-productive time.

SUMMARY

A wellbore is internally sealed using nanoparticles. Permeability properties are determined for a particular formation. A wellbore internal sealant (nanoparticle treatment fluid) is designed based on the determined permeability properties. The nanoparticle treatment fluid is introduced into the formation. Pore throats within the formation are plugged by nanoparticles in the nanoparticle treatment fluid. Permanent internal sealing reduces the leak-off from filtercake damage, and also eliminates the build-up of surface filtercake, enhancing cement bonding. A specific nanoparticle treatment fluid that seals the pore-structure of a particular wellbore zone can alleviate the need for additional lost circulation material, resulting in a very thin filtercake and significantly reducing the chance of differential sticking. Expensive and environmentally challenging oil-based muds can be replaced with water-based equivalents. The nanoparticle treatment fluid results in a permanent reduction in formation permeability, and therefore is particularly suitable for wells that will be stimulated using perforations, matrix acidizing, or fracturing techniques to re-establish hydrocarbons access through the internal barrier.

This summary is provided to introduce a selection of concepts that are further described below in the detailed description. This summary is not intended to identify key or essential features of the claimed subject matter, nor is it intended to be used as an aid in limiting the scope of the claimed subject matter.

BRIEF DESCRIPTION OF THE DRAWINGS

The present disclosure is best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion. Embodiments are described with reference to the following figures. The same numbers are generally used throughout the figures to reference like features and components.

DETAILED DESCRIPTION

It is to be understood that the following disclosure provides many different embodiments, or examples, for implementing different features of various embodiments. Specific examples of components and arrangements are described below to simplify the present disclosure. These are, of course, merely examples and are not intended to be limiting. In addition, the present disclosure may repeat reference numerals and/or letters in the various examples. This repetition is for the purpose of simplicity and clarity and does not in itself dictate a relationship between the various embodiments and/or configurations discussed. Moreover, the formation of a first feature over or on a second feature in the description that follows may include embodiments in which the first and second features are formed in direct contact, and may also include embodiments in which additional features may be formed interposing the first and second features, such that the first and second features may not be in direct contact.

Some embodiments will now be described with reference to the figures. Like elements in the various figures may be referenced with like numbers for consistency. In the following description, numerous details are set forth to provide an understanding of various embodiments and/or features. However, it will be understood by those skilled in the art that some embodiments may be practiced without many of these details and that numerous variations or modifications from the described embodiments are possible. As used here, the terms "above" and "below", "up" and "down", "upper" and "lower", "upwardly" and "downwardly", and other like terms indicating relative positions above or below a given point or element are used in this description to more clearly describe certain embodiments. However, when applied to equipment and methods for use in wells that are deviated or horizontal, such terms may refer to a left to right, right to left, or diagonal relationship, as appropriate. It will also be understood that, although the terms first, second, etc. may be used herein to describe various elements, these elements should not be limited by these terms. These terms are only used to distinguish one element from another.

The terminology used in the description herein is for the purpose of describing particular embodiments only and is not intended to be limiting. As used in the description and the appended claims, the singular forms "a", "an" and "the" are intended to include the plural forms as well, unless the context clearly indicates otherwise. It will also be understood that the term "and/or" as used herein refers to and encompasses any and all possible combinations of one or more of the associated listed items. It will be further understood that the terms "includes," "including," "comprises," and/or "comprising," when used in this specification, specify the presence of stated features, integers, steps, operations, elements, and/or components, but do not preclude the presence or addition of one or more other features, integers, steps, operations, elements, components, and/or groups thereof.

As used herein, the term "if" may be construed to mean "when" or "upon" or "in response to determining" or "in response to detecting," depending on the context. Similarly, the phrase "if it is determined" or "if [a stated condition or event] is detected" may be construed to mean "upon determining" or "in response to determining" or "upon detecting [the stated condition or event]" or "in response to detecting [the stated condition or event]," depending on the context.

A system and method to seal a wellbore is disclosed. In at least one embodiment, a wellbore internal sealant (WIS) is used to seal a formation internally at the pore-throat scale. Permanent internal sealing reduces the leak-off from filtercake damage. This may allow the traditional placement of casing sections to be altered by removing the constraint of controlling fluid leak-off. Permanent internal sealing also eliminates or reduces the build-up of surface filtercake, allowing for easier cementing preparation and stronger bonding. Designing a specific WIS to seal the pore-structure of a particular wellbore zone (i.e., formation) can alleviate or even eliminate the need for additional lost circulation material, resulting in a very thin filtercake and significantly reducing the chance of differential sticking. Oil-based muds are known for their ability to form a thinner, more effective filtercake compared to water-based muds, but with effective internal sealing it is possible to replace expensive and environmentally challenging oil-based muds with water-based equivalents.

Figure 1:
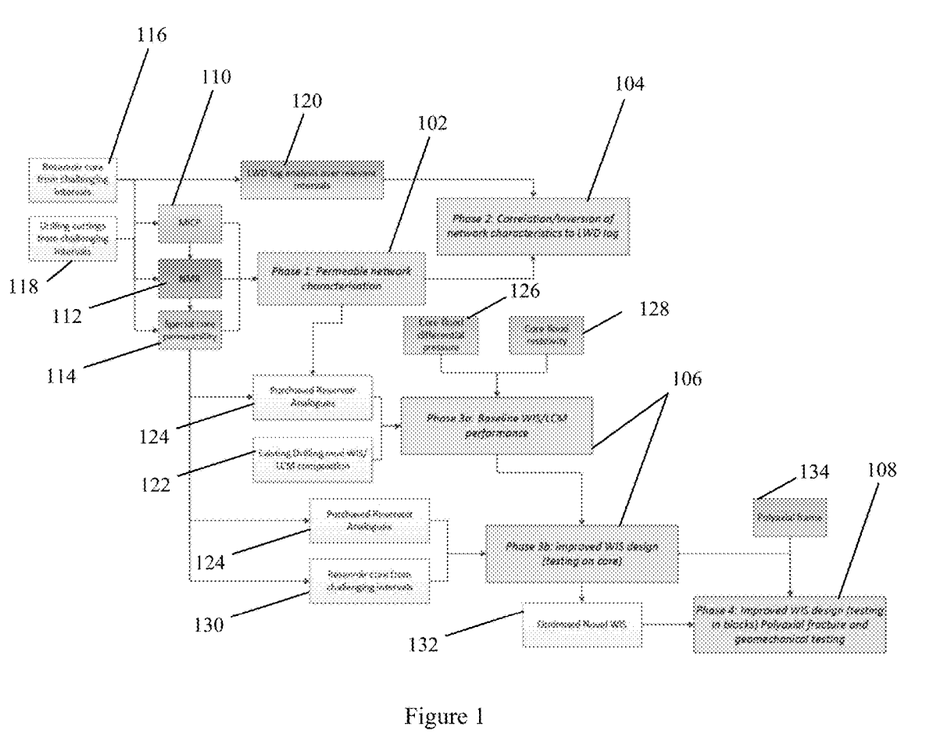
FIG. 1 is a workflow to design an appropriate particle size distribution or collection of monodisperse distributions for loading a treatment fluid, in accordance with the present disclosure.

The modified drilling fluid can be designed to act on a range of formation characteristics. In particular, it may be designed to block or plug a specific range of pore-throat diameters found in very specific target intervals. An example workflow is shown in FIG. 1. The workflow may be used to design an appropriate particle size distribution or collection of monodisperse distributions for loading the fluid. The use of nanoparticles allows such particles to penetrate into the porous media, blocking an intended range of pore-throats internally, without forming an external (i.e., wellbore wall surface) filtercake.

FIG. 1 shows four primary workflow phases. The four phases are identified as: pore-network characterization 102; correlation 104; core testing 106; and stimulation testing 108. The pore-network characterization phase 102 (Phase 1) may use, for example, alone or in combination, mercury injection capillary pressure (MICP) 110, nuclear magnetic resonance (NMR) 112, or liquid permeability laboratory measurements 114 to characterize the pore-network characteristics of the relevant wellbore intervals. Such analyses may be performed on, for example, reservoir cores 116 or drilling cuttings 118 from challenging wellbore intervals. Those determined pore-network characteristics may be used to establish the optimal distribution of particle sizes for the drilling fluid for the formation or range of formations of interest.

The logging tool correlation phase 104 (Phase 2) allows one to detect the formation or range of formations of interest. That, in turn, allows the mud composition to be efficiently and effectively modified when unexpected lithofacies are encountered as part of the natural heterogeneity present in most formations. In most wells, logging-while-drilling (LWD) tools are used to provide real-time data to the drilling team to aid geosteering and formation evaluation. LWD log analysis 120 may be performed over relevant intervals.

In at least one embodiment, an NMR tool and/or a neutron density (ND) tool are deployed to characterize the pore-network of a formation. The NMR tool provides a lithology-independent measure of porosity, pore body-size, permeability, and the mobile versus immobile fluid volume distribution in wellbores. The ND tool provides a real-time apparent neutron porosity, formation bulk density, and photoelectric factor to characterize both porosity and lithology while drilling, and can be deployed in a wide range of wellbore sizes.

The correlation phase 104 correlates the response of the drilling tool(s) to the relevant intervals by correlating to the pore-network characteristics, thereby building a library of tool responses to pore-network characteristics. That library may be used to improve the detectability of regions of specific interest such as where lost circulation and/or stuck-pipe events are prevalent.

The core testing phase 106 (Phase 3) actually comprises two sub-phases, 3a and 3b. Sub-phase 3a uses laboratory techniques to analyze the performance of a baseline WIS mixture (or existing lost circulation material) 122 in relevant reservoir cores or reservoir analogues 124 that are chosen due to their availability and having pore-network characteristics similar to the relevant formation intervals. Tests may include core flood differential pressure 126 or core flood resistivity 128. This testing, combined with the characterization techniques identified above, identifies the pore-networks that remain permeable after imbibition of existing mixtures, thereby allowing the particle size distribution to be modified to suit the reservoir intervals. This modified mixture is then tested in sub-phase 3b to ensure the desired sealing performance is achieved. In sub-phase 3b the reservoir analogues 124 or reservoir core 130 may be tested and, based on those tests, an optimized novel WIS 132 is produced.

The stimulation testing phase 108 (Phase 4) assesses the impact of the WIS 132 on a particular stimulation technique of interest. A function of the modified drilling fluid is to permanently seal the wellbore against fluid ingress. Phase 4 is used to determine whether, for example, fracture stimulation, matrix stimulation, or jetting/perforating past the damaged region will be employed to restore connection between the wellbore and hydrocarbon-bearing formation. This appears in the workflow of FIG. 1 as geomechanical testing within a polyaxial frame 134, but could alternatively be, for example, core-flood testing for matrix stimulations. Fracturing is specifically mentioned here as this is a common stimulation type, but is not meant to be limiting. As near-wellbore leak-off is reduced, an apparent increase in fracture initiation pressures is expected. Characterizing this increase allows one to design the stimulation process in harmony with the drilling process, typically termed "drill to frac" for wells that will be fractured. For example, where it is determined that the wellbore strengthening effect is higher than desirable, the stimulation team can insert a wellbore cleanup phase. For example, hydraulic jetting may be used to cut past the damaged zones. This is preferable to discovering the strengthening effect during the fracture stimulation process itself, resulting in non-productive time (NPT) due to an unplanned operation. This may also allow one to locate fracture initiation positions to better target stimulation intervals along the wellbore.

Virtually any thermally and chemically stable nanoparticle composition that can be produced in volume such as inorganic compounds of silica, carbon, titanium dioxide, and cerium oxide, or organic compounds such as nanocrystalline cellulose (NCC) may be used. These particles can be produced by a variety of techniques, such as flame hydrolysis, sol-gel processes, and acid hydrolysis, and in a variety of monodisperse or narrow size distributions. Careful control of the particle size distribution allows for more targeted fluid design. In addition, the nanoparticles may be functionalized so as to allow subsequent detection and location. That is, a marker can be fixed to the nanoparticles using specific elements or compounds that have characteristic signatures or properties. For example, gadolinium or lithium are sensitive to neutron irradiation, and manganese would be detectable by NMR by very sharply reducing the T2 response.

As stated above, at least some of the embodiments disclosed herein may be used to prevent differential sticking and to enhance the casing spacing and cementing operations during wellbore construction. Specific features are described below using, for ease of discussion, NCC as an example material, but are not limited to NCC. The shape and size of the NCC can be designed to match the pore-network characteristics of specific permeable regions using a combination of common laboratory techniques. A low concentration of NCC can be employed to produce a permanent, internal blockage in the region proximate the wellbore wall (e.g., one to three inches away from the wellbore wall), thereby affecting the permeability of the formation across that region. Thus, the nanoparticle laden fluid typically results in a permanent reduction in formation permeability, and therefore is particularly suitable for wells that will be stimulated using perforations, matrix acidizing, or fracturing techniques.

The NCC laden fluid makes a low permeability barrier without producing a thick filtercake, significantly reducing the risk of differential sticking. A thin, yet effective filtercake facilitates the switch from expensive oil-based muds, known for their superior filtercake properties, to significantly cheaper and environmentally easier water-based muds. The NCC laden fluid may be weighted to handle higher formation pressures, but also may be used to make a low viscosity fluid with minimal density increase, allowing for operation near the hydrostatic pressure of water if desired. The NCC laden fluid has low erosion properties and can pass through, for example, mud modulators and turbines without causing undue damage. Permanent internal sealing in upper wellbore construction can reduce the fluid leak-off in a more effective manner than that involving the formation of a wellbore wall filtercake, potentially increasing the length that can be drilled without casing. The absence of a surface filtercake enhances the cementing operation of casing, as the cleanup process is significantly reduced and well integrity is increased by enhancing the bonding.

A hydrocarbon-bearing region of a wellbore may remain uncased or without a bridge-seal as part of a strategy whereby one deliberately "pre-seals" the wellbore region. This would allow more precise control of the regions from which production is obtained. Another mode of operation is to seal off regions above the hydrocarbon-bearing formation. That allows an operator to keep drilling for longer distances without increasing the risk of differential sticking. Generally casing is eventually set in those regions for wellbore stability or accumulated leak-off control. However, fewer casing runs allow an operator to drill a smaller diameter hole than would be required otherwise. That is because, while a length of a given casing diameter is set inside the hole, once that casing is set (i.e., that region is sealed), the operator continues by drilling a smaller diameter hole beyond that point. Hence, for example, an operator using conventional drilling methods may need to set four or five casing diameters (due to the limited run distance before risking differential sticking), but an operator using the sealing techniques disclosed herein may need to set only two or three casing diameters.

Various operational modes are possible. For example, a WIS could be provided continuously, in quasi-real-time, or in true real-time. With a continuous feed the WIS material may be used as a low-level sealant, which allows one to adopt and adapt an overall lost-circulation strategy based on reducing leak-off, not just in high risk regions, but over the entire wellbore length. In quasi-real-time, continuous analysis of returned cuttings on the rig-site could help determine which of a number of "pre-selected" combinations of WIS particle distributions that are generally sufficient and ready to be included into the drilling mud at a moments notice would be most suitable for a particular application.

Because the treatment is generally effective at low total concentrations, true real-time application can also be achieved. Concentrations as low as 1% are often adequate to create an effective seal. Thus, a small section of drillstring/bottomhole assembly can be preloaded with sufficient WIS material (e.g., several kg) that can be released on command and delivered immediately to the drill-bit, being mixed, for example, into the drilling fluid by the turbulence through the turbines. This can either bring about the desired end result or buy enough time to load up the mud appropriately to deal with the impending issue. The release command could be by manual control or occur automatically using a controller (e.g., built into the LWD tools on the string). The immediacy of the action reduces an operator's needed reaction time and can trigger an alarm to sooner initiate a recovery response.

Figure 2:
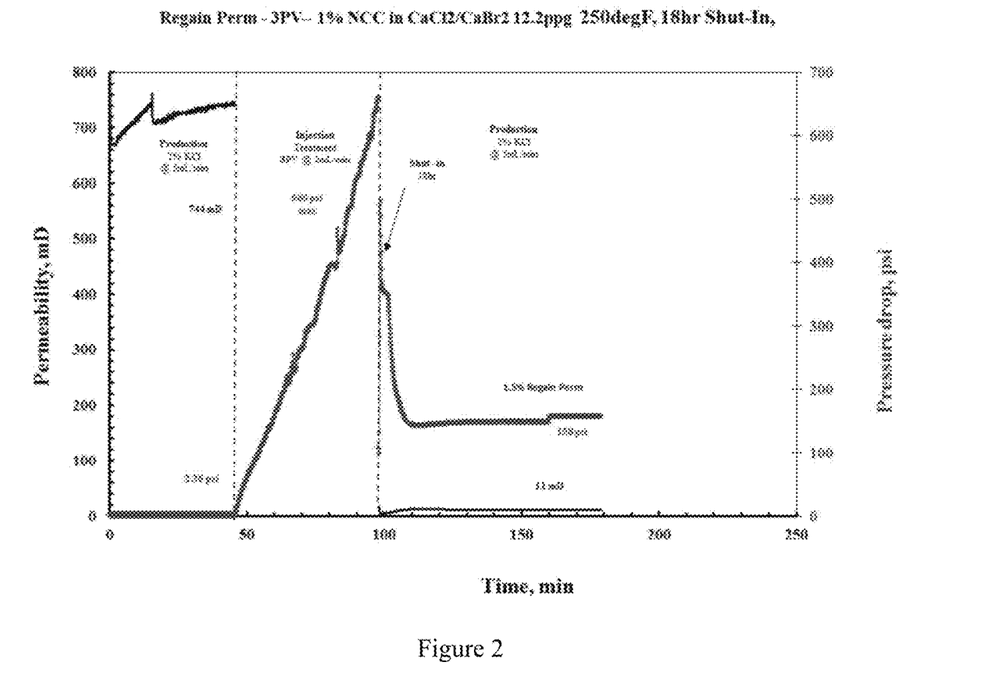
FIG. 2 is a plot showing, for one sample, the permeability, pressure drop, and recovered permeability from counter flow as functions of time, in accordance with the present disclosure.

In one tested embodiment, nanocrystalline cellulose with a length of about 100 nm and a diameter of about six nm was dispersed in an approximate 1% by weight brine solution ($CaCl_2/CaBr_2$ 12.2 pounds per gallon (ppg)). To determine the extent of formation plugging, a measurement of the permeability of a core sample before and after introduction of a treatment fluid was performed (three pore volume, flow rate less than or equal to 2 ml/min). The testing was done at 250° F. The initial and final core permeability was measured using a 2% KCl solution. FIG. 2 is a plot showing the permeability and pressure drop as functions of time. The initial permeability of the core was measured to be 744 mD (flow rate less than or equal to five ml/min). After introduction of the treatment fluid and a shut-in time of approximately 18 hours, the permeability of the core was down to 11 mD. (The data taken during shut-in of 18-hr is not included as there is no flow of fluid during that time. The data taken after the shut-in is plotted as a continuation to show the low injectivity next to the initial injectivity.) As shown in FIG. 2, the introduction of the nanocrystalline cellulose into the relatively high permeability core created pore plugging.

Figure 3:
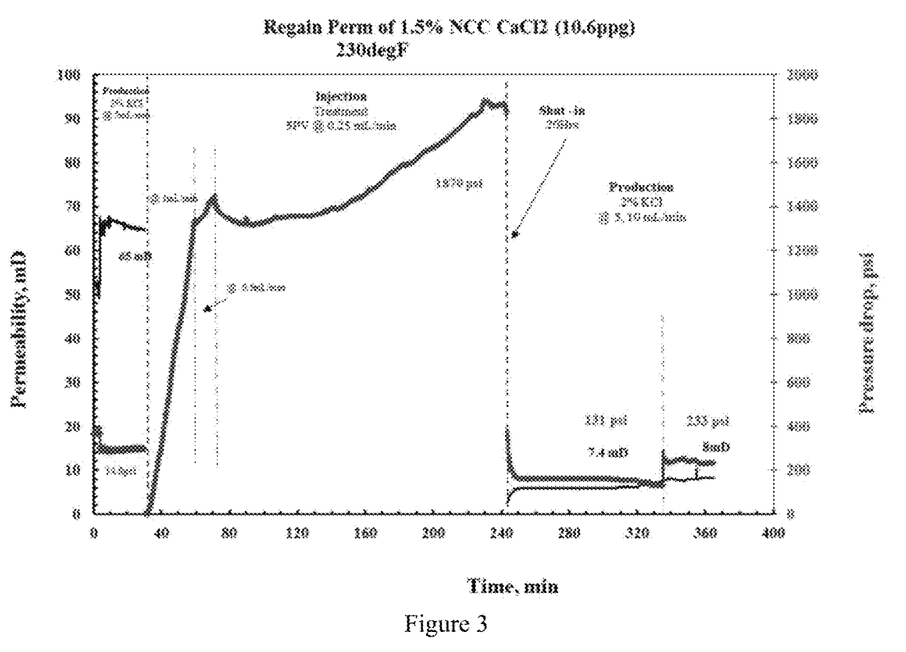
FIG. 3 is a plot showing, for another sample, the permeability, pressure drop, and recovered permeability from counter flow as functions of time, in accordance with the present disclosure.

In an alternate tested embodiment on a lower permeability core, a solution of $CaCl_2$ (10.6 ppg) containing 1.5% by weight NCC (five pore volume) was introduced into a low permeability core. As before, the initial and final core permeability was measured using a 2% KCl solution. Results of the permeability measurement are shown in FIG. 3, as are the details of the treatment. The initial permeability was measured to be 65 mD. After treatment fluid introduction, 8 mD was measured. The temperature of the experiment was set at 230° F. These results show that the nanoparticles penetrated the formation and plugged the small pores, preventing further flow through the core sample.

Figure 4:
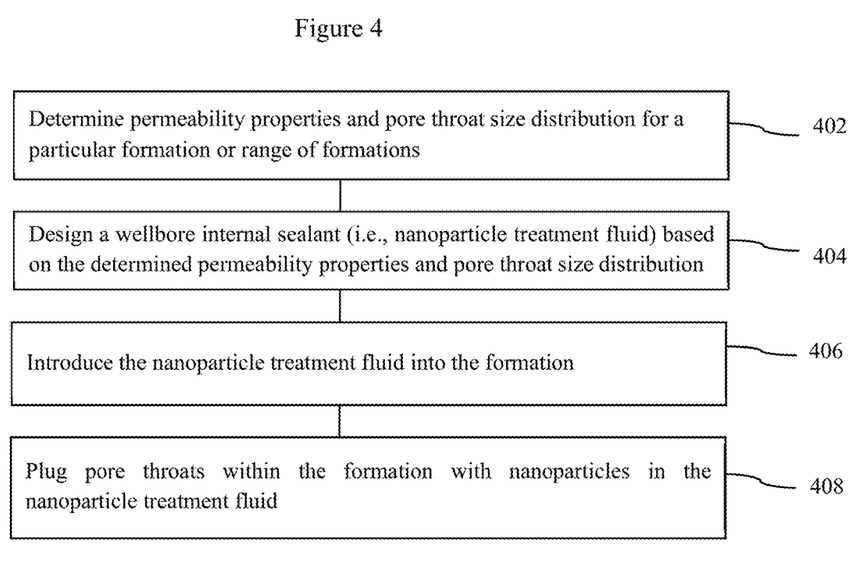
FIG. 4 is a workflow showing an embodiment of sealing a wellbore, in accordance with the present disclosure.

FIG. 4 is a flowchart showing one embodiment of internally sealing a wellbore. Permeability properties and pore throat size distribution are determined for a particular formation or range of formations (402). A wellbore internal sealant (i.e., nanoparticle treatment fluid) is designed based on the determined permeability properties (404). The nanoparticle treatment fluid is introduced into the formation (406). Pore throats within the formation are plugged by nanoparticles in the nanoparticle treatment fluid (408).

The foregoing outlines features of several embodiments so that those skilled in the art may better understand the aspects of the present disclosure. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the scope of the present disclosure, and that they may make various changes, substitutions, and alterations herein without departing from the scope of the present disclosure.

The Abstract at the end of this disclosure is provided to comply with 37 C.F.R. § 1.72(b) to allow the reader to quickly ascertain the nature of the technical disclosure. It is submitted with the understanding that it will not be used to interpret or limit the scope or meaning of the claims.

While only certain embodiments have been set forth, alternatives and modifications will be apparent from the above description to those skilled in the art. These and other alternatives are considered equivalents and within the scope of this disclosure and the appended claims. Although only a few example embodiments have been described in detail above, those skilled in the art will readily appreciate that many modifications are possible in the example embodiments without materially departing from this invention. Accordingly, all such modifications are intended to be included within the scope of this disclosure as defined in the following claims. In the claims, means-plus-function clauses are intended to cover the structures described herein as performing the recited function and not only structural equivalents, but also equivalent structures. Thus, although a nail and a screw may not be structural equivalents in that a nail employs a cylindrical surface to secure wooden parts together, whereas a screw employs a helical surface, in the environment of fastening wooden parts, a nail and a screw may be equivalent structures. It is the express intention of the applicant not to invoke 35 U.S.C. § 112, paragraph 6 for any limitations of any of the claims herein, except for those in which the claim expressly uses the words 'means for' together with an associated function.

What is claimed is:

1. A method, comprising:
    determining permeability properties and pore throat size distribution of a formation penetrated by a wellbore wherein determining permeability properties comprises analyzing a core sample or formation drilling cuttings and wherein the analyzing comprises using one or more techniques selected from the group consisting of: mercury injection capillary pressure (MICP), nuclear magnetic resonance (NMR), and liquid permeability laboratory measurements;
    designing a nanoparticle treatment fluid based on the determined permeability properties and pore throat size distribution;
    introducing the nanoparticle treatment fluid into the formation; and
    plugging pore throats in the formation with nanoparticles in the nanoparticle treatment fluid, thereby producing an internally sealed formation.

2. The method of claim 1, further comprising leaving wellbore sections surrounded by the internally sealed formation uncased.

3. The method of claim 1, wherein the nanoparticle treatment fluid is water-based.

4. The method of claim 1, further comprising:
    producing a thin external filtercake on the wellbore wall surface adjacent to the internally sealed formation.

5. The method of claim 1, wherein designing a nanoparticle treatment fluid comprises estimating an optimal particle size distribution or collection of monodisperse distributions for loading the nanoparticle treatment fluid.

6. The method of claim 1, wherein designing a nanoparticle treatment fluid comprises correlating logging-while-drilling data with the determined permeability properties.

7. The method of claim 1, wherein designing a nanoparticle treatment fluid comprises analyzing a baseline wellbore internal sealant mixture.

8. The method of claim 7, wherein the analyzing is done using a reservoir core or a reservoir analogue.

9. The method of claim 7, further comprising:
    modifying the particle size distribution of the baseline wellbore internal sealant based on the results of the analysis.

10. The method of claim 1, wherein designing a nanoparticle treatment fluid comprises performing stimulation testing to select a stimulation technique.

11. The method of claim 10, wherein the stimulation technique is selected from a group consisting of: fracture stimulation, matrix stimulation, and jetting/perforating past a damaged region in the wellbore.

12. The method of claim 1, wherein the nanoparticle treatment fluid comprises a nanoparticle composition selected from a group consisting of: compounds of silica, carbon, titanium dioxide, cerium oxide, and nanocrystalline cellulose.

13. The method of claim 1, further comprising:
enhancing casing spacing in the wellbore.

14. The method of claim 1, further comprising conditioning the wellbore to avoid differential sticking.

15. A method, comprising:
determining permeability properties and pore throat size distribution of a formation penetrated by a wellbore wherein determining permeability properties comprises analyzing a core sample or formation drilling cuttings and wherein the analyzing comprises using one or more techniques selected from the group consisting of: mercury injection capillary pressure (MICP), nuclear magnetic resonance (NMR), and liquid permeability laboratory measurements;
designing a nanoparticle treatment fluid based on the determined permeability properties and pore throat size distribution;
sealing a subsurface formation penetrated by a wellbore by introducing the nanoparticle treatment material into the formation; and
holding a volume of nanoparticle treatment material in reserve within a drillstring or bottomhole assembly, and, upon command, releasing the nanoparticle treatment material, thereby effecting the seal in real-time.

16. The method of claim 15, further comprising:
selecting a stimulation zone.

17. The method of claim 15, further comprising:
enhancing a wellbore/casing bond in a cementing operation.

18. The method of claim 15, further comprising:
functionalizing the nanoparticle treatment material to allow for subsequent detection and/or location.

19. The method of claim 15, wherein the introducing a nanoparticle treatment material into the formation is done continuously, in quasi-real-time, or in true real-time.

* * * * *